United States Patent
Min et al.

(10) Patent No.: US 9,402,688 B2
(45) Date of Patent: Aug. 2, 2016

(54) SURGICAL ROBOT SYSTEM AND CONTROL METHOD THEREOF

(71) Applicant: SAMSUNG ELECTRONICS CO., LTD., Suwon-si, Gyeonggi-do (KR)

(72) Inventors: Seung Ki Min, Hwaseong-si (KR); Kyung Shik Roh, Seongnam-si (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 0 days.

(21) Appl. No.: 14/162,338

(22) Filed: Jan. 23, 2014

(65) Prior Publication Data

US 2014/0324070 A1 Oct. 30, 2014

(30) Foreign Application Priority Data

Apr. 30, 2013 (KR) .................. 10-2013-0048317

(51) Int. Cl.
*G05B 19/04* (2006.01)
*A61B 19/00* (2006.01)
*A61B 17/00* (2006.01)

(52) U.S. Cl.
CPC ... *A61B 19/2203* (2013.01); *A61B 2017/00123* (2013.01)

(58) Field of Classification Search
USPC .......... 700/245, 260, 246, 250, 247; 600/424, 600/130, 118, 170, 111
See application file for complete search history.

(56) References Cited

U.S. PATENT DOCUMENTS

| | | | | |
|---|---|---|---|---|
| 5,784,542 A * | 7/1998 | Ohm et al. | ..................... | 700/260 |
| 6,233,504 B1 * | 5/2001 | Das | ..................... | A61B 19/2203 414/4 |
| 6,424,885 B1 * | 7/2002 | Niemeyer | ............... | A61B 19/22 600/109 |
| 6,963,792 B1 * | 11/2005 | Green | ................. | A61B 1/00193 348/E13.014 |
| 7,155,316 B2 * | 12/2006 | Sutherland | .............. | A61B 19/22 318/568.11 |
| 7,371,210 B2 * | 5/2008 | Brock | ................ | A61B 17/0469 600/114 |
| 7,608,083 B2 * | 10/2009 | Lee | ..................... | A61B 17/0469 606/1 |
| 7,689,320 B2 * | 3/2010 | Prisco et al. | ................... | 700/245 |
| 7,775,972 B2 * | 8/2010 | Brock | ................ | A61B 17/0469 600/114 |
| 8,398,541 B2 * | 3/2013 | DiMaio et al. | ................ | 600/111 |
| 8,414,598 B2 * | 4/2013 | Brock | ................ | A61B 19/2203 606/130 |
| 8,600,551 B2 * | 12/2013 | Itkowitz et al. | ................ | 700/245 |
| 8,620,473 B2 * | 12/2013 | Diolaiti | .............. | A61B 19/2203 600/407 |
| 9,101,397 B2 * | 8/2015 | Guthart | ................... | A61B 19/22 |
| 9,119,654 B2 * | 9/2015 | Ramans | ............. | A61B 19/2203 |
| 2008/0221591 A1 * | 9/2008 | Farritor | ............ | A61B 17/00234 606/130 |
| 2010/0274087 A1 * | 10/2010 | Diolaiti et al. | ................ | 600/118 |
| 2011/0041160 A1 | 2/2011 | Choi | | |
| 2011/0264136 A1 * | 10/2011 | Choi | .................. | A61B 19/2203 606/205 |
| 2012/0071752 A1 * | 3/2012 | Sewell et al. | .................. | 600/424 |
| 2014/0005708 A1 * | 1/2014 | Shelton, IV | ................... | 606/170 |
| 2014/0316430 A1 * | 10/2014 | Hourtash | ..................... | 606/130 |

FOREIGN PATENT DOCUMENTS

| | | |
|---|---|---|
| JP | 2004-338057 | 12/2004 |
| KR | 10-2010-0008946 | 1/2010 |
| KR | 10-2012-0061499 | 6/2012 |

* cited by examiner

*Primary Examiner* — Ronnie Mancho
(74) *Attorney, Agent, or Firm* — Harness, Dickey & Pierce, P.L.C.

(57) ABSTRACT

A surgical robot system and a control method thereof include a slave device and a master device to control motion of the slave device. The surgical robot system further includes a monitoring device that inspects a signal transmitted within the system in real time to stop motion of the slave device if an abnormal signal is detected.

19 Claims, 7 Drawing Sheets

SURGICAL ROBOT SYSTEM AND CONTROL METHOD THEREOF

CROSS-REFERENCE TO RELATED APPLICATIONS

This application claims the priority benefit of Korean Patent Applications No. 10-2013-0048317, filed on Apr. 30, 2013 in the Korean Intellectual Property Office, the disclosure of which is incorporated herein by reference.

BACKGROUND

1. Field

Embodiments disclosed herein relate to a surgical robot system that monitors signals transmitted within the system to prevent malfunction of a slave device and a control method thereof.

2. Description of the Related Art

Minimally invasive surgery generally refers to surgical methods which may minimize the size of an incision. Different from laparotomy, which uses a relatively larger surgical incision through a part of a human body (e.g., the abdomen), in minimally invasive surgery, an incision size is minimized. For example, in minimally invasive surgery, after forming at least one small port (or incision) of about 0.5 cm-1.5 cm through the abdominal wall, an operator inserts an endoscope and a variety of surgical instruments through the port, to perform surgery while viewing an image.

Compared to laparotomy, minimally invasive surgery has several advantages, such as lower pain after surgery, an earlier recovery, an earlier restoration of ability to eat, a shorter hospitalization, a more rapid return to daily life, and superior cosmetic effects owing to a smaller incision size relative to laparotomy procedures. Accordingly, minimally invasive surgery has been used in a variety of procedures, including gall resection, prostate cancer, and herniotomy operations, etc, and the use range thereof increasingly expands.

In general, a surgical robot system used in minimally invasive surgery includes a master device and a slave device. The master device generates a control signal corresponding to an operator's (e.g., a doctor's) manipulation to transmit the control signal to the slave device. The slave device receives the control signal from the master device to perform manipulation required for a surgical operation to be performed on a patient. The master device and the slave device may be integrated with each other, or may be separately arranged in an operating room.

The slave device generally includes at least one robot arm provided at an end thereof with a surgical instrument. In this case, each robot arm and each surgical instrument are operated in response to a control signal transmitted from the master device. If the control signal transmitted from the master device has a problem, the robot arm and the surgical instrument may malfunction, causing severe patient injury.

SUMMARY

It is an aspect of the present invention to provide a surgical robot system that secures safety during surgery and a control method thereof.

Additional aspects of the invention will be set forth in part in the description which follows and, in part, will be apparent from the description, or may be learned by practice of the invention.

In accordance with one aspect of the invention, a surgical robot system, which includes a slave device and a master device to control motion of the slave device, further includes a monitoring device that inspects a signal transmitted within the system in real time to stop a motion of the slave device if an abnormal signal is detected.

The monitoring device may include a signal collector to collect the signal transmitted within the system in real time, a signal analyzer to analyze the collected signal, and a controller to control real-time collection of the signal transmitted within the system using the signal collector and the analysis of the collected signal using the signal analyzer, and to stop the motion of the slave device if an abnormal signal is detected. The monitoring device may inspect a signal transmitted between the master device and the slave device in real time.

The monitoring device may be separated from the master device and the slave device. The monitoring device may be located inside the master device or inside the slave device. If the monitoring device is located inside the master device or inside the slave device a power source unit may be connected to the monitoring device. The power source unit connected to the monitoring device may not provide power to the master device and the slave device.

The controller may be configured to, suitable for, capable of, adapted to, etc., monitor periodic communication between the master device and the slave device and to stop motion of the slave device if periodic communication is not detected.

The slave device may include a plurality of drive units to drive a plurality of joints of a robot arm and a plurality of joints of a surgical instrument and an emergency brake unit to interrupt power to be applied to the plurality of drive units. The controller of the monitoring device may control interruption of power to be applied to the plurality of drive units using the emergency brake unit to stop the motion of the slave device.

The monitoring device may further include a communication unit and a brake signal generator to generate a brake signal to stop the motion of the slave device. The controller may transmit the brake signal to the slave device via the communication unit to stop the motion of the slave device. The controller of the slave device may transmit a drive signal to the plurality of drive units of the slave device to operate the robot arm and the surgical instrument, and the controller of the monitoring device may inspect the drive signal in real time and interrupt power to be applied to the plurality of drive units via the emergency brake unit if an abnormal drive signal is detected to stop the motion of the slave device.

In accordance with another aspect of the invention, a control method of a surgical robot system, the surgical robot system including a slave device and a master device to control motion of the slave device, includes collecting a signal transmitted within the system, judging whether or not the collected signal is normal via analysis of the signal, and stopping motion of the slave device if the signal is judged to be abnormal.

Judgment of whether or not the collected signal is normal via analysis of the signal may includes judging whether the signal is a normal signal or an abnormal signal and judging whether the master device and the slave device periodically communicate with each other. The stopping of the motion of the slave device may be implemented by interrupting power to be applied to a drive unit that drives at least one joint of the slave device.

In accordance with another aspect of the invention, a monitoring device connected to a master device and a slave device or a surgical robot, includes a signal collector to collect a signal generated by at least one of the master device or slave device, a signal analyzer to analyze the collected signal, and a controller to stop a motion of the slave device if an abnormal signal is detected based on the analysis of the collected signal. The monitoring device may further include a brake signal generator to generate a brake signal to stop a motion of the slave device if an abnormal signal is detected.

The controller of the monitoring device may selectively stop a motion of the slave device according to whether it is determined a controller of the slave device has malfunctioned. If it is determined the controller of the slave device has not malfunctioned, the controller of the monitoring device may transmit a brake signal generated by the brake signal generator to the slave device to direct the controller of the slave device to stop the motion of the slave device. If it is determined the controller of the slave device has malfunctioned, the controller of the monitoring device may directly control an emergency brake unit of the slave device to interrupt power applied to at least one drive unit of the slave device, to stop the motion of the slave device. The controller may determine whether communication is periodically performed between the master device and slave device, and may stop a motion of the slave device if the periodic communication is not performed.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
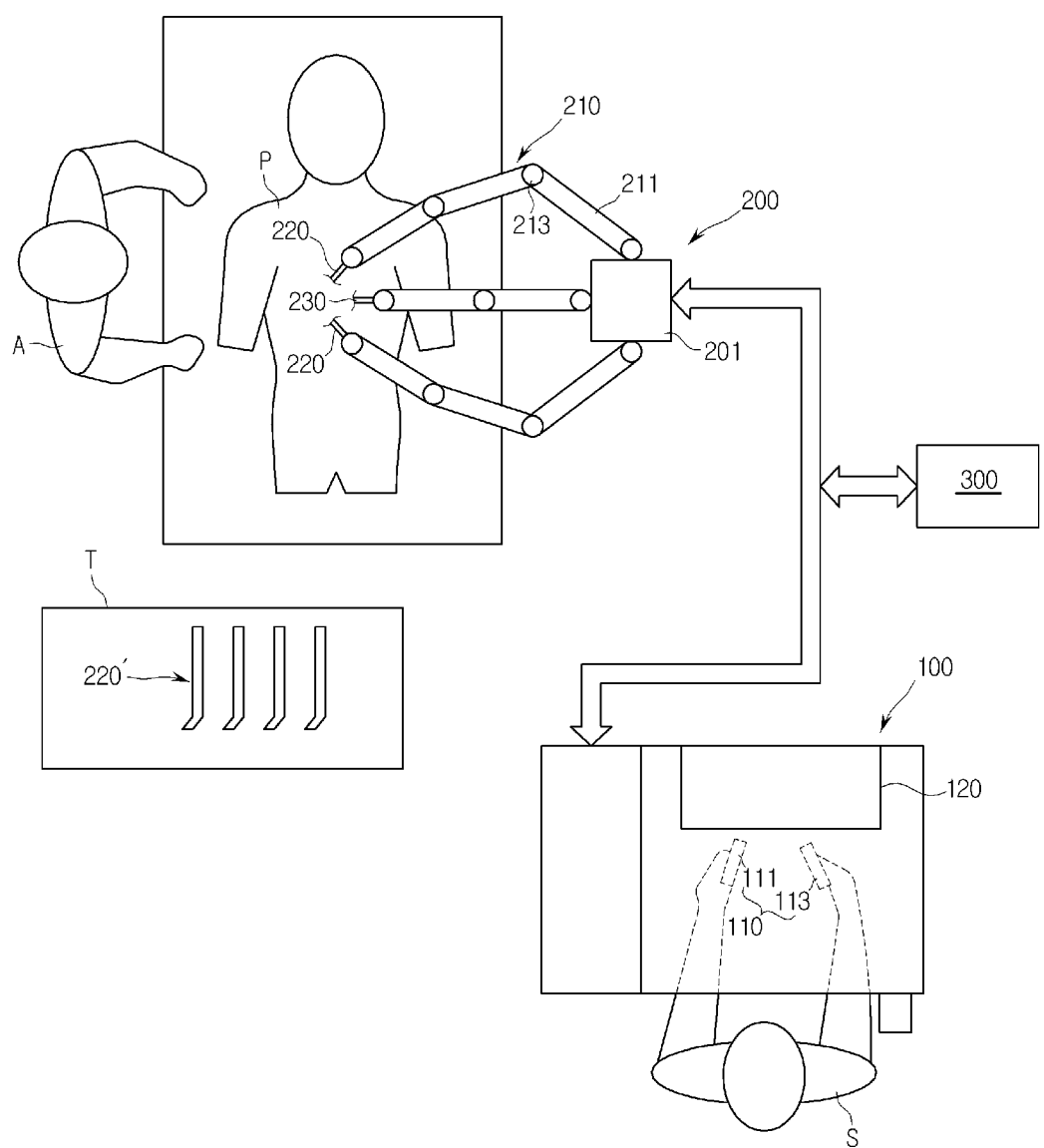
FIG. 1 is a view showing an outer appearance of a surgical robot system.

Aspects, specific advantages and novel features of the embodiments of the present invention will become apparent with reference to the following detailed description and embodiments described below in detail in conjunction with the accompanying drawings. It is noted that the same or similar elements are denoted by the same reference numerals even though they are depicted in different drawings. In addition, a detailed description of well-known techniques may be omitted to avoid unnecessarily obscuring the present disclosure. Herein, the terms first, second, etc. are used simply to discriminate any one element from other elements, and the elements are not limited to these terms.

Hereinafter, reference will now be made in detail to example embodiments of the present invention, examples of which are illustrated in the accompanying drawings, wherein like reference numerals refer to like elements throughout.

Figure 2:
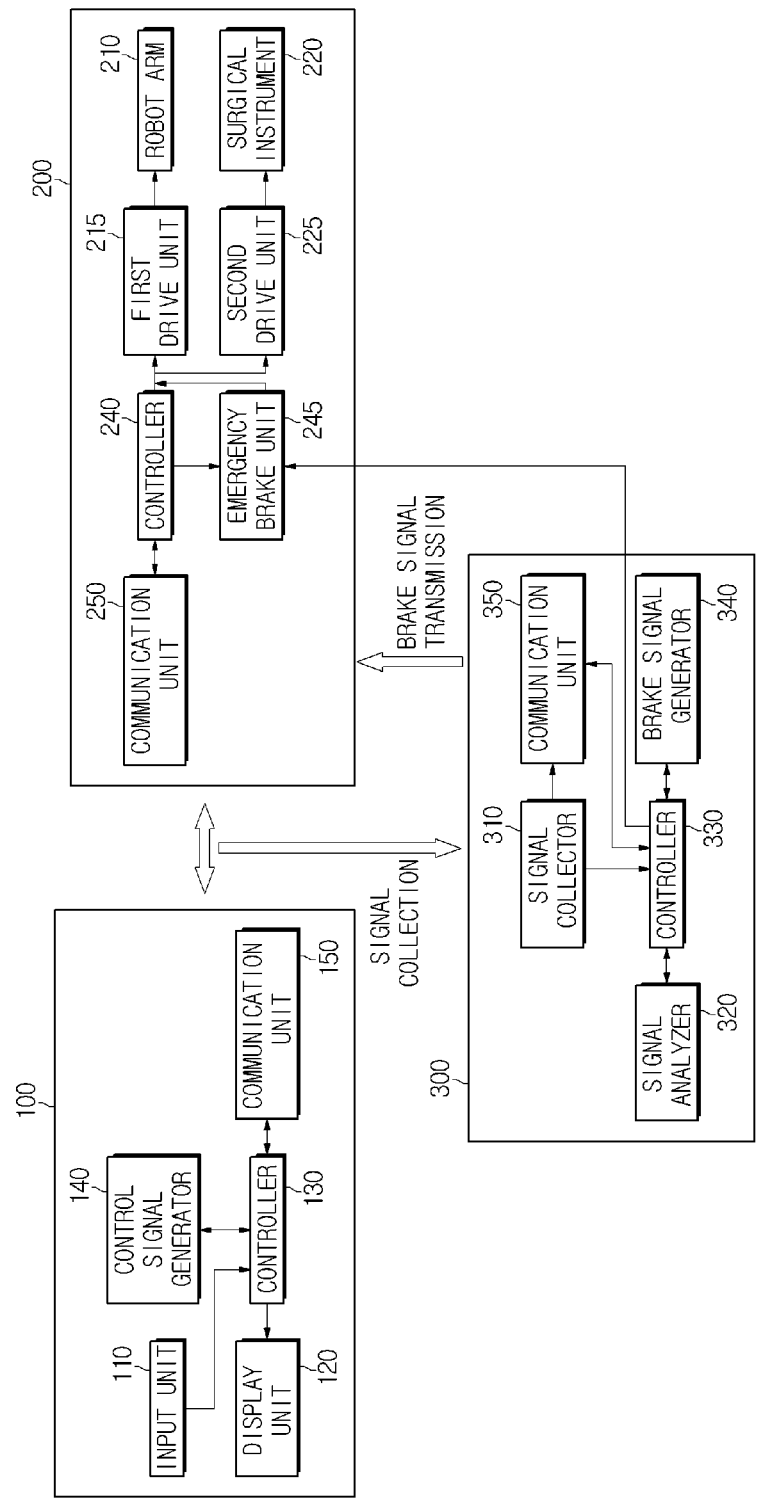
FIG. 2 is a block diagram showing one example of a configuration of the surgical robot system.

FIG. 1 is a view showing an outer appearance of a surgical robot system, and FIG. 2 is a block diagram showing an example of a configuration of the surgical robot system.

Referring to FIG. 1, the surgical robot system may include a slave device 200 which may be used to perform surgery on an object (e.g., a patient P who lies on an operating table), and a master device 100 to assist an operator S (e.g., a doctor) in remotely controlling the slave device 200. As one example, at least one assistant A who assists the operator S may be located near the patient P.

Here, assisting the operator S may refer to assisting a surgical operation or task or maneuver, and for example, may include exchanging surgical instruments disposed on an end of the robot arm of the slave device, without being in any way limited thereto. For example, since various surgical instruments may be used according to the kind of surgery and the number of robot arms 210 of the slave device 200 is limited, the number of surgical instruments 220 that are mounted at once is also limited or finite. Accordingly, when it is necessary to change the surgical instruments 220 during surgery, the operator S may instruct the assistant A near the patient P to change the surgical instruments 220, and the assistant A may remove the unnecessary surgical instrument 220 from the robot arm 210 of the slave device 200 and mount another surgical instrument 220' placed on a tray T to the corresponding robot arm 210. As another non-limiting example, the assistant may be directed by the operator to physically position or move a robot arm of the slave device during surgery, or may be directed to perform other tasks with respect to the surgical robot and/or patient.

The master device 100 and the slave device 200 may be physically separate devices, but the disclosure is not limited thereto. In one example, the master device 100 and the slave device 200 may be integrated with each other.

As exemplarily shown in FIGS. 1 and 2, the master device 100 may include an input unit 110 and a display unit 120.

The input unit 110 may receive instructions input by the operator, such as, for example, an instruction for selection of an operation mode of the surgical robot system, or an instruction for remote control of motion of the slave device 200, surgical instruments 220, and/or an endoscope 230 of the slave device 200. The input unit 110 may be embodied as one or more of a haptic device, clutch pedal, switch, button, or the like, without being in any way limited thereto. For example, a voice recognition device, keys, joystick, keyboard, mouse, touch screen, may also be used to enable a user to control the surgical robot. Thus, the input unit 110 may include at least one or a combination of input devices as disclosed herein to control the surgical robot. Hereinafter, the input unit 110 will be described as a haptic device by way of example.

Although FIG. 1 shows the input unit 110 as including two handles 111 and 113, this is merely one embodiment and the disclosure is not limited thereto. For example, the input unit 110 may include one handle, or three or more handles.

The operator may control a motion of the robot arm 210 as well as motion of the surgical instrument 220 of the slave device 200 by moving the two handles with the user's hands. Although not shown in the drawings, each handle may include a contact portion, a plurality of links, and a plurality of joints.

Here, the contact portion may refer to a portion that the operator's hand directly touches and may take the form of a pencil or stick, without being in any way limited thereto.

Each joint may serve to connect two links to each other and may have 1 degree of freedom (DOF) or more. The DOF refers to a DOF with regard to kinematics or inverse kinematics. The DOF of a mechanism refers to the number of independent motions of the mechanism, or the number of variables that determine independent motions at relative positions between links. For example, an object in a 3D space defined by X-, Y-, and Z-axes has 3 DOF to determine a spatial position of the object (a position on each axis) and/or 3 DOF to determine a spatial orientation of the object (a rotation angle relative to each axis). More specifically, it will be appreciated that an object has 6 DOF if the object is movable along each of X-, Y and Z-axes and is rotatable about each of X-, Y- and Z-axes.

The joint may be provided with a detector (not shown) to detect information regarding the state of each joint, for example, information regarding force/torque applied to the joint, information regarding a position of the joint, information regarding a movement speed of the joint, and the like. As such, if the operator manipulates the input unit 110, the detector may detect information regarding the state of the manipulated input unit 110 and transmit the detected information regarding the state of the input unit 110 to a controller 130 as shown in FIG. 2.

A control signal generator 140 of the controller 130 may generate a control signal corresponding to information regarding the state of the input unit 110 transmitted from the detector, and may transmit the control signal to the slave device 200 via a communication unit 150. The control signal may be received by the slave device 200 via a communication unit 250.

That is, the controller 130 of the master device 100 may generate a control signal corresponding to the detected state information depending on manipulation of the input unit 110 by the operator using the control signal generator 140, and may transmit the generated control signal to the slave device 200 using the communication unit 150.

The display unit 120 of the master device 100 may display, e.g., a real image collected via an endoscope 230 of the slave device 200, a virtual 3D image converted from a medical image of the patient obtained before surgery, and an augmented reality image generated by projecting the virtual image onto the real image collected via the endoscope 230. To this end, the controller 130 of the master device 100 may include an image processor (not shown) that receives image data transmitted from the slave device 200 to output the processed data to the display unit 120. Alternatively, the image processor may be disposed in the slave device 200, and image processing may be performed or carried out by the slave device 200 and results of the image processing may be transmitted to the master device 100, to be displayed for example. Here, the "image data" may include one or more of the aforementioned real image, virtual image, and augmented reality image, for example, without being in any way limited thereto.

The display unit 120 may include one or more monitors such that the respective monitors individually display information required or desired for surgery. In one example, if the display unit 120 includes three monitors, one of the monitors may display image data transmitted from the slave device 200, e.g., the aforementioned real image, virtual image and augmented reality image, and the other two monitors may respectively display information regarding motion of the slave device 200 and patient information. In this case, the number of monitors may be determined in various ways according to the type or kind of information to be displayed. That is, the number of monitors may be one or may be plural. The display unit 120 may be embodied by, for example, a Liquid Crystal Display (LCD), light emitting diode (LED) display, organic light emitting diode (OLED) display, plasma display panel (PDP), cathode ray tube (CRT), and the like.

Here, "patient information" may include information indicating the state of the patient, for example, patient vital signs, such as body-temperature, pulse, respiration-rate, blood-pressure, etc. To provide the master device 100 with the vital signs, the slave device 200 that will be described hereinafter may further include a vital sign measurement unit including a body-temperature measurement module, a pulse measurement module, a respiration-rate measurement module, a blood-pressure measurement module, etc. To this end, the controller 130 of the master device 100 may further include a signal processor (not shown) that receives and processes vital signs transmitted from the slave device 200 to output the processed vital signs to the display unit 120. Alternatively, or additionally, the master device 100 may include a device (e.g., a vital sign measurement unit and/or sensors) to measure biological information regarding the operator at the master device 100.

The slave device 200, as shown in FIG. 1 for example, may include a plurality of robot arms 210, and surgical instruments 220 mounted at ends of the respective robot arms 210. The plurality of robot arms 210, as exemplarily shown in FIG. 1, may be coupled to a body 201 so as to be fixed to and supported by the body 201. In this case, the number of the surgical instruments 220 that are used at once as well as the number of the robot arms 210 may depend on various factors, such as diagnostic methods, surgical methods, and spatial restrictions of an operating room.

Although not shown in detail in FIG. 1, each of the plurality of robot arms 210 may include a plurality of links 211 and a plurality of joints 213. Each joint may connect the two links 211 to each other and may have 1 DOF or more.

Each joint of the robot arm 210, as exemplarily shown in FIG. 2, may be provided with a first drive unit 215 to control movement of the robot arm 210 in response to a control signal transmitted from the master device 100. For example, if the operator S manipulates the input unit 110 of the master device 100, the master device 100 may generate a control signal corresponding to information regarding the state of the manipulated input unit 110 to transmit the control signal to the slave device 200. A controller 240 of the slave device 200 may transmit a drive signal corresponding to the control signal transmitted from the master device 100 to the first drive unit 215, thereby controlling movement of each joint of the robot arm 210. In this case, a practical procedure of controlling rotation and movement of the robot arm 210 in a given direction based on manipulation of the input unit 110 by the operator S would be understood by one of ordinary skill in the art, and thus a detailed description thereof will be omitted herein.

Meanwhile, although each joint of the robot arm 210 of the slave device 200 may be moved in response to a control signal transmitted from the master device 100 as described above, the joint may be moved by external force. That is, the assistant A located near an operating table may manually move each joint of the robot arm 210 so as to control, e.g., a position of the robot arm 210.

Although not shown in detail in FIG. 1, each surgical instrument 220 may include a housing mounted to the end of the robot arm 210, a shaft extending from the housing by a predetermined length, and an end effector coupled to a distal end of the shaft.

In general, the surgical instruments 220 may be classified into main surgical instruments and auxiliary surgical instruments. Here, the "main surgical instrument" may refer to an instrument including an end effector (e.g., a knife or a surgical needle) that performs direct surgical motion, such as, e.g., cutting, suturing, clotting, or washing, on a surgical region. The "auxiliary surgical instrument" may refer to an instrument including an end effector (e.g., a skin holder) that does not perform direct motion on a surgical region and assists motion of the main surgical instrument.

The shaft may include a plurality of joints to allow the surgical instrument 220 to bend via movement of the joints, which enables a pliable operation like that by real human arms. To this end, the slave device 200 may include a second drive unit 225 to control movement of the joints. For example, if the operator S manipulates the input unit 110 of the master device 100, the master device 100 may generate a control signal corresponding to information regarding the state of the manipulated input unit 110 to transmit the control signal to the slave device 200. The controller 240 of the slave device 200 may transmit a drive signal corresponding to the control signal transmitted from the master device 100 to the second drive unit 215, thereby controlling movement of each joint of the surgical instrument 210.

The end effector may refer to a part of the surgical instrument 220 that practically acts on a surgical region of the patient P. For example, the end effector may include a skin holder, suction line, knife, scissors, grasper, surgical needle, staple applier, needle holder, scalpel, cutting blade, etc., without being in any way limited thereto. Any other instruments required for surgery may be used. The surgical tools or instruments may also include, for example, a, micro-dissector, tacker, suction irrigation tool, clip applier, irrigator, catheter, suction orifice, surgical knife, surgical forceps, a cautery (a tool for burning or cutting a diseased part by using electric energy or heat energy), and the like.

The endoscope 230 may serve to assist the motion of a main surgical instrument rather than directly performing surgical motion on a surgical region. Thus, it will be appreciated that the endoscope 230 corresponds to an auxiliary surgical instrument in a broad sense. The endoscope 230 may be selected from among various surgical endoscopes, such as a thoracoscope, arthroscope, rhinoscope, cystoscope, proctoscope, duodenoscope, and cardioscope, in addition to a celioscope that is mainly used in robotic surgery. In addition, the slave device 200 may further include a drive unit (not shown) to drive the endoscope 230 such that the endoscope 230 is moved to an image capture region and captures an image.

The slave device 200 may further include a display unit (not shown) to display a real image collected via the endoscope 230 and a 3D virtual image converted from medical images of the patient before surgery.

The master device 100 and the slave device 200 may construct a network. In this case, the network may be a wired network, a wireless network, or a combination thereof. The master device 100 and the slave device 200 may receive and transmit signals via the network.

For example, the master device 100 may transmit a control signal to the slave device 200 via the network. Here, the "control signal" may include a control signal for position adjustment and operation of the surgical instruments 220 of the slave device 200 and a control signal for position adjustment and operation of the endoscope 230, without being in any way limited thereto. In this case, if it is necessary to transmit the respective control signals simultaneously or at similar times, the respective control signals may be transmitted independently of each other. For example, the respective control signals may be transmitted in parallel. Additionally, or alternatively, the respective control signals may be transmitted at a substantially similar time sequentially.

Here, "independent" transmission of the respective control signals may refer to no interference between the control signals, and also refer to that any one control signal has no effect on the other control signal. To ensure independent transmission of the plurality of control signals, various methods may be used. For example, header information may be added per control signal upon generation of each control signal, control signals may be transmitted based on a generation sequence thereof, or control signals may be transmitted based on a preset order of priority.

The slave device 200 may transmit a feedback signal indicating a drive state based on a control signal transmitted from the master device 100 to the master device 100 via the network. In addition, the slave device 200 may transmit signals indicating the aforementioned vital signs, such as body-temperature, pulse, respiration-rate, blood-pressure, etc., to the master device 100 via the network. As such, transmission and/or reception of various signals, such as audio, video, control and feedback signals, may be implemented between the master device 100 and the slave device 200, and each device may be operated in response to the received signal and output the received signal.

Numerous signals including control and feedback signals may be transmitted in the form of a packet in a network. Here, the "packet" may refer to the unit of data that is segmented for easy transmission via a network, and may include a header part and a data part. The header part may include information regarding a destination of the packet, data identification information, and the like.

As described above, in the general surgical robot system, the slave device 200 may be operated in response to a control signal transmitted from the master device 100 as the operator S manipulates the master device 100. If the master device 100 transmits an erroneous control signal, or the controller 240 of the slave device 200 transmits an erroneous drive signal to the respective drive units for the robot arm 210 and the surgical instrument 220, i.e. the first drive unit 215 and the second drive unit 225, the robot arm 210 and the surgical instrument 220 of the slave device 200 may malfunction, causing severe patient injury.

Therefore, in an embodiment, to secure safety during surgery, as exemplarily shown in FIG. 1, a monitoring device 300 may be provided, which inspects signals transmitted within the system in real time to detect an erroneous abnormal signal, and stops motion of the slave device 200 if the abnormal signal is detected. The monitoring device 300 according to the present embodiment may be present in the same network as the master device 100 and the slave device 200. That is, the monitoring device 300 may communicate with the master device 100 and slave device 200 over a wired network, a wireless network, or a combination thereof.

More specifically, the monitoring device 300 according to the present embodiment, as exemplarily shown in FIG. 2, may include a signal collector 310 that collects signals transmitted within the system in real time, a signal analyzer 320 that analyzes the collected signals, and a controller 330 that controls the collection of signals using the signal collector 310 as well as the analysis of the collected signals using the signal analyzer 320, and stops motion of the slave device 200 upon detection of an abnormal signal.

Here, the "signals" may refer mainly to signals with regard to motion of the slave device 200. The signals may include a motion control signal transmitted from the master device 100 to the slave device 200, a feedback signal transmitted from the slave device 200 to the master device 100, and a drive signal transmitted from the controller 240 of the slave device 200 to the first drive unit 215 and/or the second drive unit 225, without being in any way limited thereto.

In an example embodiment, the monitoring device 300 may inspect a motion control signal and a feedback signal transmitted between the master device 100 and the slave device 200, and may stop the motion of the slave device 200 if an abnormal signal is detected. In another exemplary embodiment, the monitoring device 300 may inspect a drive signal transmitted from the controller 240 of the slave device 200 to one or more drive units (e.g., plural or all) of the slave device 200. The monitoring device may interrupt power to be applied to one or more of the drive units if an abnormal signal is detected to thereby stop a motion of the slave device 200. For example, the monitoring device 300 may inspect a drive signal transmitted from the controller 240 of the slave device 200 to any one of the respective drive units 215 and 225, and interrupt power to be applied to one or more of the drive units 215 and 225 if an abnormal signal is detected to thereby stop a motion of the slave device 200.

Hereinafter, the above embodiments will be described respectively in more detail.

In an embodiment, the surgical robot system, as exemplarily shown in FIG. 2, may include the monitoring device 300, which is separated from the master device 100 and the slave device 200 and is located outside (externally) of the system. That is, the monitoring device 300 may be physically disposed away from the slave device and master device. The monitoring device 300 may inspect a signal transmitted between the master device 100 and the slave device 200 in real time to detect an abnormal signal, and may stop a motion of the slave device 200 if an abnormal signal is detected. In this case, the signal inspected by the monitoring device 300 may be the aforementioned motion control signal and feedback signal, without being in any way limited thereto.

More specifically, the controller 330 of the monitoring device 300 according to the present embodiment may control collection of a motion control signal and a feedback signal transmitted between the master device 100 and the slave device 200 in real time using the signal collector 310, and then control analysis of the collected motion control signal and feedback signal using the signal analyzer 320. Then, the controller 330 may judge or determine whether the collected motion control signal and feedback signal are normal signals or abnormal signals. If the signals are judged or determined to be abnormal, the controller 330 may stop a motion of the slave device 200 to prevent the slave device 200 from malfunctioning in response to the abnormal signals.

In addition, the controller 330 of the monitoring device 300 may inspect whether or not the master device 100 and the slave device 200 periodically perform communication. If periodic communication is not performed, the controller 330 may judge or determine that the slave device 200 or the master device 100 has a problem, and may stop a motion of the slave device 200. For example, the periodic communication may refer to communication at predetermined intervals (e.g., scheduled intervals), or communication within a predetermined amount of time.

For example, to stop a motion of the slave device 200, a method of transmitting a brake signal to the slave device 200 and a method of directly interrupting power to be applied to the respective drive units 215 and 225 of the slave device 200 may be adopted.

Among the aforementioned methods, to stop the motion of the slave device 200 by transmitting the brake signal to the slave device 200, the monitoring device 300, as exemplarily shown in FIG. 2, may include a brake signal generator 340 and a communication unit 350. Here, the "brake signal" may refer to a signal that controls an emergency brake unit 245 of the slave device 200 to interrupt power to be applied to the respective drive units 215 and 225, without being in any way limited thereto. For example, the controller 330 of the monitoring device 300 may transmit a brake signal generated by the brake signal generator 340 to the slave device 200 via the communication unit 350, and the controller 240 of the slave device 200 may control the emergency brake unit 245 in response to the transmitted brake signal to interrupt power to be applied to the respective drive units 215 and 225, thereby stopping motion of the slave device 200.

In addition, or alternatively, the monitoring device 300 may directly interrupt power to be applied to the respective drive units 215 and 225 of the slave device 200 to provide against malfunction of the controller 240 of the slave device 200. That is, the controller 330 of the monitoring device 300 may directly control the emergency brake unit 245 of the slave device 200 so as to interrupt power to be applied to the respective drive units 215 and 225.

The controller 330 of the monitoring device 300 may selectively adopt the aforementioned methods to stop a motion of the slave device 200 according to various circumstances. For example, if an abnormal motion control signal transmitted from the master device 100 to the slave device 200 is detected, the controller 330 may judge that the master device 100 has a problem. Thus, the controller 300 may transmit a brake signal to the slave device 200 so as to stop a motion of the slave device 200. Conversely, if an abnormal feedback signal transmitted from the slave device 200 to the master device 100 is detected, the controller 330 may judge that the slave device 200 has a problem and the controller 240 of the slave device 200 is not normally operated. Thus, the controller 330 may directly control the emergency brake unit 245 of the slave device 200 to interrupt power to be applied to the respective drive units 215 and 225, thereby stopping motion of the slave device 200.

Figure 3:
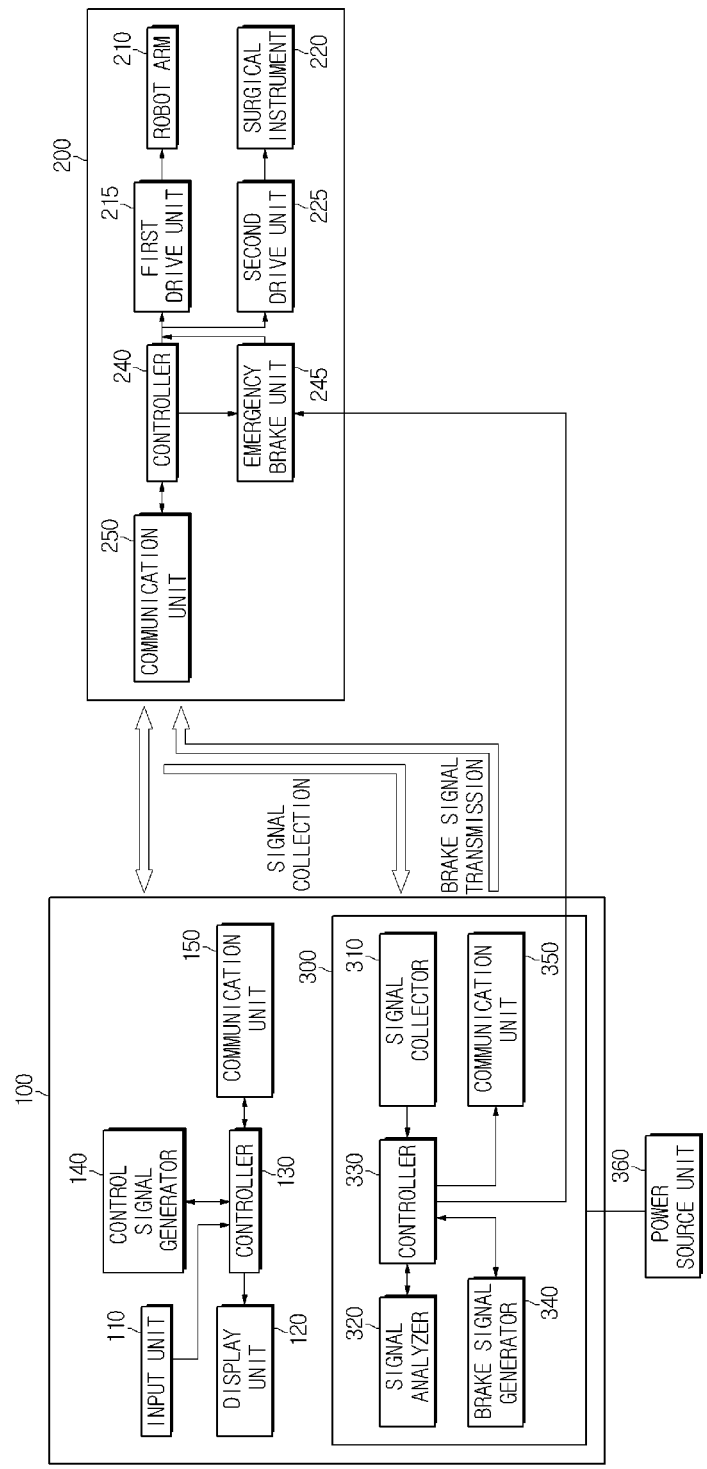
FIG. 3 is a block diagram showing a configuration of the surgical robot system in which a monitoring device is located inside a master device.
Figure 4:
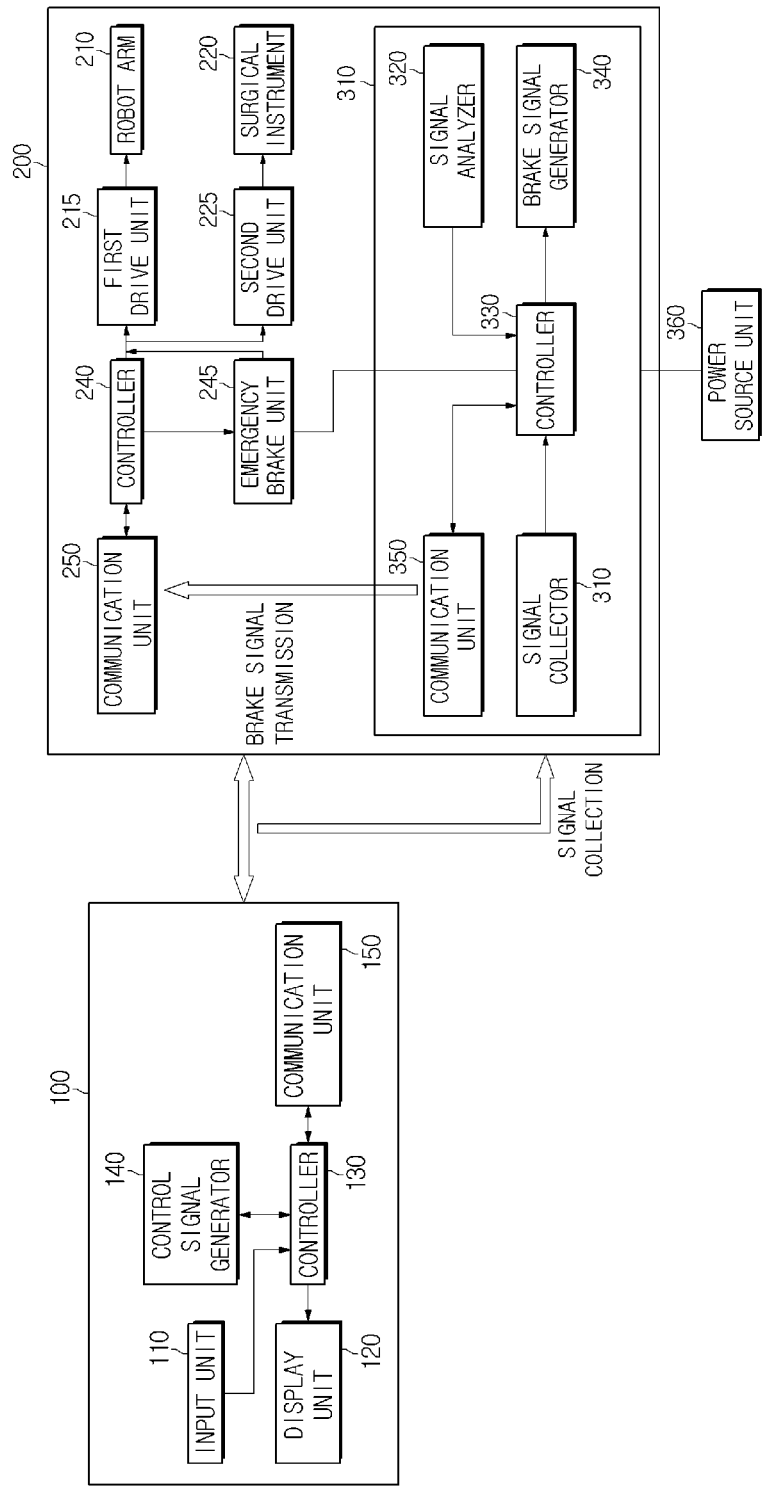
FIG. 4 is a block diagram showing a configuration of the surgical robot system in which a monitoring device is located inside a slave device.

Different from the aforementioned configuration or arrangement, in the surgical robot system according to an embodiment, the monitoring device 300 may be located inside the master device 100 as exemplarily shown in FIG. 3, or may be located inside the slave device 200 as exemplarily shown in FIG. 4.

Accordingly, the surgical robot system may further include a separate power source unit 360 connected to the monitoring device 300. If the monitoring device 300 located inside the master device 100 is connected to the same power source unit as that of the master device 100, or if the monitoring device 300 located inside the slave device 200 is connected to the same power source unit as that of the slave device 200, the monitoring device 300 may be affected by unintentional power-off of the master device 100 and the slave device 200, and this may make it impossible to stop motion of the slave device 200 in an emergency situation. However, through provision of the separate power source unit 360, the monitoring device 300 may be normally operated even if the master device 100 or the slave device 200 has a problem. By way of example, the separate power source unit 360 may include a battery power supply, DC power supply, AC power supply, or a combination thereof, as would be understood by one of ordinary skill in the art.

As described above, in the surgical robot system according to the firstly described embodiment, the monitoring device 300 may inspect a signal transmitted between the master device 100 and the slave device 200 in real time, and immediately stop a motion of the slave device 200 as soon as an abnormal signal is detected.

Figure 5:
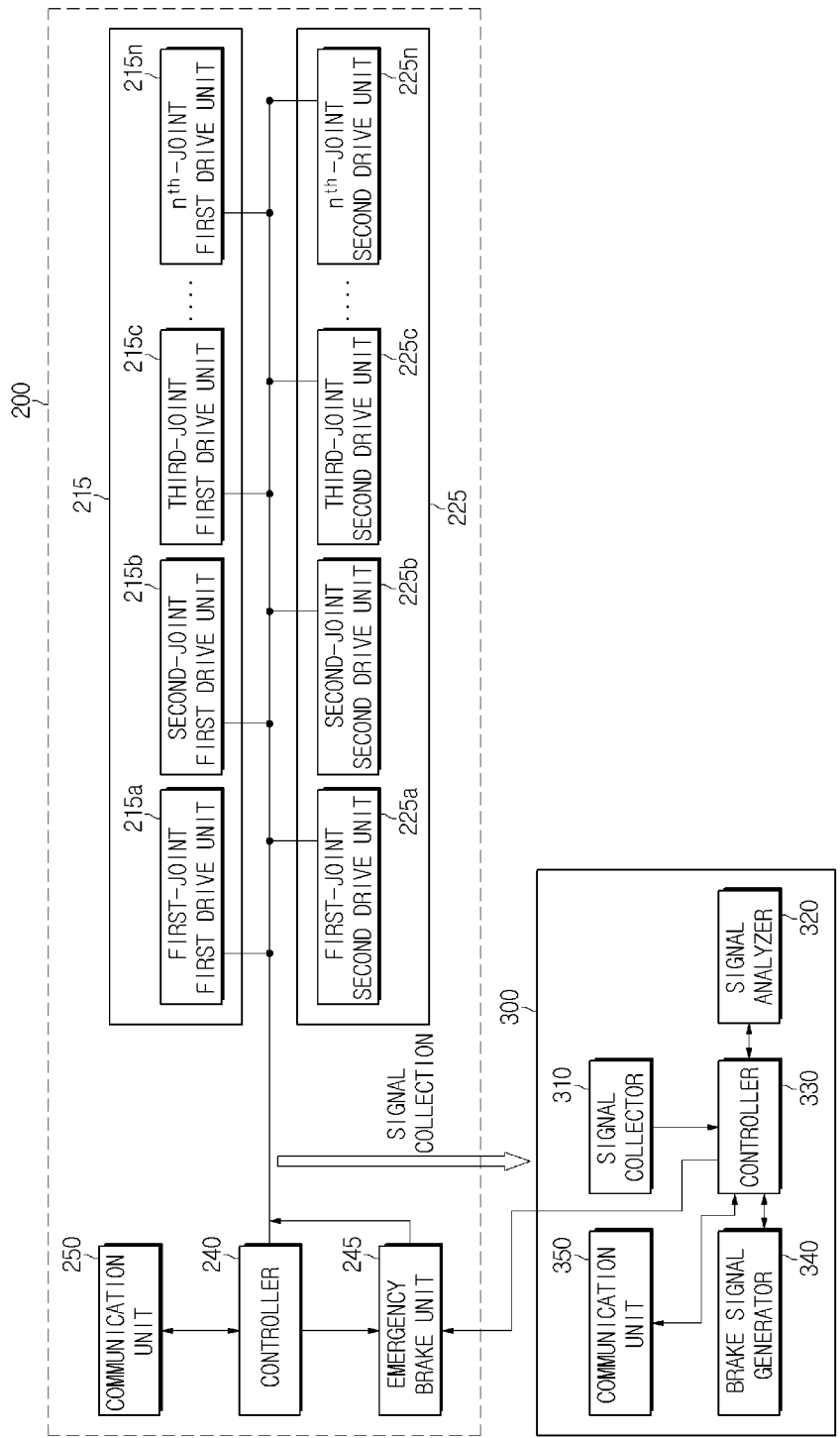
FIG. 5 is a block diagram showing another example of a configuration of the surgical robot system.

The surgical robot system according to an embodiment, as shown in FIG. 5 for example, may include the monitoring device 300, which inspects drive signals transmitted from the controller 240 of the slave device 200 to the respective drive units 215 and 225 in real time, and directly controls the emergency brake unit 245 of the slave device 200 to interrupt power to be applied to the respective drive units 215 and 225 if an abnormal signal is detected, thereby stopping motion of the slave device 200.

The slave device 200, as described above, may include the plurality of robot arms 210 and the surgical instruments 220 mounted to the ends of the respective robot arms 210. In addition, each of the robot arms 210 and each of the surgical instruments 220 may include a plurality of joints, and may further include the first drive unit 215 to drive the joints of the robot arm 210 and the second drive unit 225 to drive the joints of the surgical instrument 220.

In this case, as exemplarily shown in FIG. 5, a plurality of first drive units 215 and a plurality of second drive units 225 may be provided. For example, if the robot arm 210 includes a plurality of joints from a first-joint to an nth joint, the first drive units 215, as exemplarily shown in FIG. 5, may include a first-joint first drive unit 215a to drive a first joint, a second-joint first drive unit 215b to drive a second joint, a third-joint first drive unit 215c to drive a third joint, and an nth-joint first drive unit 215n to drive an nth joint, without being in any way limited thereto. In addition, if the surgical instrument 220 includes a plurality of joints from a first joint to an nth joint, the second drive units 225, as exemplarily shown in FIG. 5, may include a first-joint second drive unit 225a to drive a first joint, a second-joint second drive unit 225b to drive a second joint, a third-joint second drive unit 225c to drive a third joint, and an nth-joint second drive unit 225n to drive an nth joint, without being in any way limited thereto.

FIG. 5 shows the monitoring device 300 as being located outside the slave device 200 (for example, located inside of the master device 100 or externally to both the slave device 200 and master device 100), but the monitoring device 300 is not in any way limited thereto, and may be located inside the slave device 200 as exemplarily shown in FIG. 4. If the monitoring device 300 is located inside the slave device 200, as described above, the separate power source unit 360 connected to the monitoring device 300 may be provided.

In an embodiment, the monitoring device 300, as described above, may inspect a drive signal transmitted from the controller 240 to the respective drive units 215 and 225 in real time. The monitoring device 300 may judge an abnormal operation of the controller 240 if an abnormal drive signal is detected, and immediately interrupt power to be applied to the respective drive units 215 and 225 under control of the emergency brake unit 245 to prevent motion of the robot arm 210 and the surgical instrument 220.

As described above, the monitoring device 300 of the surgical robot system according to the example embodiments disclosed herein, may be constructed as an external device present in the same network as the master device 100 and the slave device 200 to monitor and analyze signals transmitted between the master device 100 and the slave device 200. The monitoring device may be easily constructed without substantially requiring modifications of the master device 100 and the slave device 200. This ensures simplified configurations of the master device 100 and the slave device 200 because the number of modules of the master device 100 and the slave device 200 is not increased despite provision of the monitoring device 300, resulting in enhanced device safety.

Figure 6:
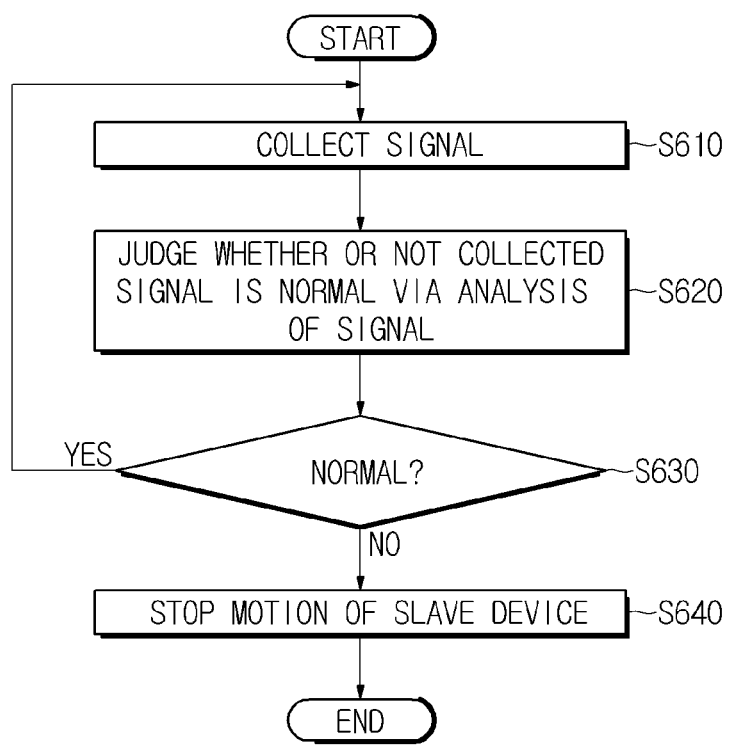
FIG. 6 is a flowchart schematically showing a control method of the surgical robot system.

FIG. 6 is a flowchart schematically showing a control method of the surgical robot system.

Referring to FIG. 6, first, a signal transmitted within the system is collected (S610), and the collected signal is analyzed so that a determination or judgment may be made as to whether or not the signal is normal (S620). If the signal is judged abnormal (S630), motion of the slave device 200 is stopped (S640).

In this case, the signal collected in operation S610 may be a signal transmitted between the master device 100 and the slave device 200, or a signal transmitted from the controller 240 of the slave device 200 to the respective drive units 215 and 225, although the disclosure is not in any way limited thereto. That is, according to the example embodiments disclosed herein, the signal transmitted between the master device 100 and the slave device 200 may be monitored in real time to stop motion of the slave device 200 if an abnormal signal is detected, or the signal transmitted from the controller 240 of the slave device 200 to the respective drive units 215 and 225 may be monitored in real time to stop motion of the slave device 200 if an abnormal signal is detected.

For example, motion of the slave device 200 may be stopped by interrupting power to be applied to the respective drive units 215 and 225 that drive the respective joints of the robot arms 210 and the surgical instruments 220 of the slave device 200, although the disclosure is not in any way limited thereto. Alternatively, stopping motion of the slave device 200 may refer to stopping all motion of the slave device 200. That is, all components (e.g., robot arms, surgical instruments, joints thereof, etc.) of the slave device 200 which may be moving, about to move, or potentially could be moved, may be stopped by interrupting power to all drive units that drive respective joints of the robot arms and surgical instruments of the surgical robot. Or, for example, stopping motion of the slave device 200 may refer to stopping all motion of a component (e.g., robot arm, surgical instrument, joints thereof, etc.) associated with the control signal for which the control signal has been determined to be abnormal. For example, if a control signal associated with moving a first instrument is determined to be abnormal, then all motion associated with that component may be stopped. For example, the first instrument, robot arm to which the first instrument is attached, and joints thereof, may be prevented from moving by interrupting power to the drive units which correspond to the first instrument and the robot arm which the first instruments is attached to. Meanwhile, other portions of the slave device 200 may be permitted to operate.

A motion of the slave device 200 may be stopped for a predetermined amount of time, until the abnormality is resolved, according to a user or default setting, and the like.

Figure 7:
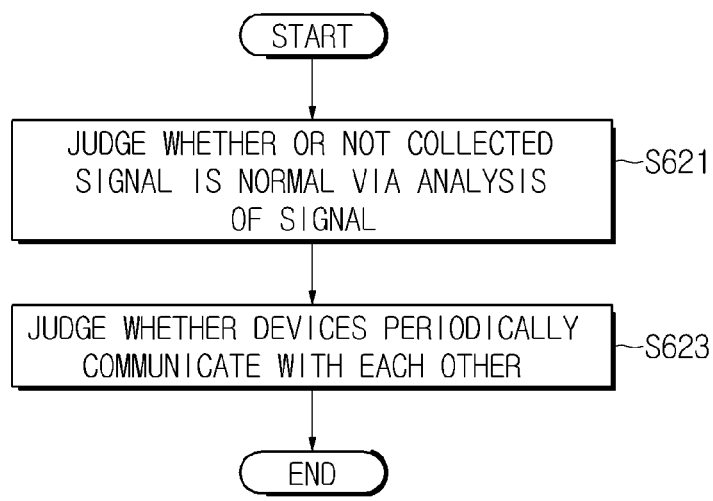
FIG. 7 is a flowchart showing details of operation S620 of FIG. 6.

A determination or judgment of whether or not the signal is normal via analysis of the signal S620, as exemplarily shown in FIG. 7, may include judging whether the collected signal is a normal signal or abnormal signal (S621), and judging whether or not the respective devices, i.e. the master device 100 and the slave device 200 periodically communicate with each other (S623). Thereafter, if the collected signal is judged abnormal, motion of the slave device 200 is stopped so as to prevent malfunction upon receiving an abnormal signal. In addition, if the master device 100 and the slave device 200 do not periodically communicate with each other, the master device 100 and the slave device 200 may be judged as having a problem and motion of the slave device 200 may be stopped based on the judgment of an abnormal situation. In this way, it may be possible to prevent surgical accidents and to secure safety during surgery.

A minimally invasive surgical robot and control method thereof according to the example embodiments disclosed herein are not limited to the surgical robot disclosed herein. For example, the surgical robot and control method thereof may also be applied to settings other than a medical environment. For example, the surgical robot and control method thereof according to the example embodiments may be utilized to perform operations in any confined space or enclosure in which an operator may need to perform controlled movements using an instrument attached to a robot arm, so as to avoid or to prevent injuries to bodies or objects, that may be located or disposed within the space or enclosure, due to imprecise movements of the robot. The surgical robot and control method thereof according to the example embodiments may be applied to, for example, mining operations, surveillance operations, inspection operations, repair operations, bomb disposal operations, etc., however again, the disclosure is not so limited. Further, while the operator of a surgical robot may be a doctor, the operator generally may be any user, and need not be a doctor.

The apparatus and methods according to the above-described example embodiments may use one or more processors. For example, a processing device may be implemented using one or more general-purpose or special purpose computers, such as, for example, a processor, an image processor, a controller and an arithmetic logic unit, a central processing unit (CPU), a graphics processing unit (GPU), a digital signal processor (DSP), a microcomputer, a field programmable array, a programmable logic unit, an application-specific integrated circuit (ASIC), a microprocessor or any other device capable of responding to and executing instructions in a defined manner.

The terms "module", and "unit," as used herein, may refer to, but are not limited to, a software or hardware component or device, such as a Field Programmable Gate Array (FPGA) or Application Specific Integrated Circuit (ASIC), which performs certain tasks. A module or unit may be configured to reside on an addressable storage medium and configured to execute on one or more processors. Thus, a module or unit may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and modules/units may be combined into fewer components and modules/units or further separated into additional components and modules.

Some example embodiments of the present disclosure can also be embodied as a computer readable medium including computer readable code/instruction to control at least one component of the above-described example embodiments. The medium may be any medium that can storage and/or transmission the computer readable code.

Aspects of the above-described example embodiments may be recorded in non-transitory computer-readable media including program instructions to implement various operations embodied by a computer. The media may also include, alone or in combination with the program instructions, data files, data structures, and the like. The program instructions recorded on the media may be those specially designed and constructed for the purposes of the example embodiments, or they may be of the kind well-known and available to those having skill in the computer software arts. Examples of non-transitory computer-readable media include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. The media may be transfer media such as optical lines, metal lines, or waveguides including a carrier wave for transmitting a signal designating the program command and the data construction. Examples of program instructions include both machine code, such as produced by a compiler, and files containing higher level code that may be executed by the computer using an interpreter. The described hardware devices may be configured to act as one or more software modules in order to perform the operations of the above-described example embodiments, or vice versa. In addition, a non-transitory computer-readable storage medium may be distributed among computer systems connected through a network and computer-readable codes or program instructions may be stored and executed in a decentralized manner. In addition, the computer-readable storage media may also be embodied in at least one application specific integrated circuit (ASIC) or Field Programmable Gate Array (FPGA). Some or all of the operations performed according to the above-described example embodiments may be performed over a wired or wireless network, or a combination thereof.

Each block of the flowchart illustrations may represent a unit, module, segment, or portion of code, which comprises one or more executable instructions for implementing the specified logical function(s). It should also be noted that in some alternative implementations, the functions noted in the blocks may occur out of the order. For example, two blocks shown in succession may in fact be executed substantially concurrently or the blocks may sometimes be executed in the reverse order, depending upon the functionality involved. Also, while an illustration may show an example of the direction of flow of information for a process, the direction of flow of information may also be performed in the opposite direction for a same process or for a different process.

Although example embodiments of the present invention have been shown and described, it would be appreciated by those skilled in the art that changes may be made to these embodiments without departing from the principles and spirit of the invention, the scope of which is defined in the claims and their equivalents.

What is claimed is:

1. A surgical robot system comprising:
    a slave device configured to generate drive signals based on a control signal, and transmit the drive signals to a plurality of drive units based on the drive signals;
    a master device configured to control a motion of the slave device by transmitting the control signal thereto; and
    a monitoring device including,
        a signal collector configured to collect the control signal and the drive signals transmitted within the system in real time,
        a signal analyzer configured to analyze the control signal and the drive signals in real time to detect if any of the control signal and the drive signals are abnormal, and
        a controller configured to control real-time collection of the control signal and the drive signals and analysis thereof, and to stop the motion of the slave device, if the controller detects that one or more of the control signal and the drive signals are abnormal, wherein the signal collector, the signal analyzer and the controller of the monitoring device are electrically connected together.

2. The system according to claim 1, wherein the monitoring device inspects a signal transmitted between the master device and the slave device in real time.

3. The system according to claim 2, wherein the monitoring device is separated from the master device and the slave device.

4. The system according to claim 2, wherein the monitoring device is located inside the master device or inside the slave device.

5. The system according to claim 4, further comprising a power source unit connected to the monitoring device.

6. The system according to claim 2, wherein the controller is adapted to monitor periodic communication between the master device and the slave device and to stop motion of the slave device if periodic communication is not detected.

7. The system according to claim 6 wherein the slave device includes:
the plurality of drive units to drive a plurality of joints of a robot arm and a plurality of joints of a surgical instrument; and
an emergency brake unit to interrupt power to be applied to the plurality of drive units, and
wherein the controller controls interruption of power to be applied to the plurality of drive units using the emergency brake unit to stop the motion of the slave device.

8. The system according to claim 1, wherein the monitoring device further includes:
a communication unit; and
a brake signal generator to generate a brake signal to stop the motion of the slave device, and
wherein the controller transmits the brake signal to the slave device via the communication unit to stop the motion of the slave device.

9. The system according to claim 1, wherein the slave device includes:
the plurality of drive units to drive a plurality of joints of a robot arm and a plurality of joints of a surgical instrument;
an emergency brake unit to interrupt power to be applied to the plurality of drive units; and
a controller to transmit the drive signals to the plurality of drive units to operate the robot arm and the surgical instrument, and
wherein the controller of the monitoring device inspects the drive signals in real time and interrupts power to be applied to the plurality of drive units via the emergency brake unit if an abnormal drive signal is detected to stop the motion of the slave device.

10. The system according to claim 9, wherein the monitoring device is located inside or outside the slave device.

11. The system according to claim 10, further comprising a power source unit connected to the monitoring device if the monitoring device is located inside the slave device.

12. A control method of a surgical robot system, the surgical robot system including a slave device, a master device and a monitoring device, the method comprising:
analyzing, by the monitoring device, a control signal and drive signals, the control signal being transmitted from the master device to the slave device, and the drive signals being transmitted from the slave device to a plurality of drive units associated therewith;
determining whether one or more of the control signal and the drive signals are abnormal based on the analyzing and
stopping a motion of the slave device if the monitoring device detects that one or more of the control signal and the drive signals are abnormal, wherein the monitoring device includes,
a signal collector configured to collect the control signal and the drive signals transmitted within the system in real time,
a signal analyzer configured to analyze the control signal and the drive signals in real time to detect if any of the control signal and the drive signals are abnormal, and
a controller configured to control real-time collection of the control signal and the drive signals and analysis thereof, and to stop the motion of the slave device, if the controller detects that one or more of the control signal and the drive signals are abnormal, wherein the signal collector, the signal analyzer and the controller of the monitoring device are electrically connected together.

13. The method according to claim 12, wherein judgment of whether the determining includes:
determining whether one or more of the control signal and the drive signals are normal signals or abnormal signals; and
determining whether the master device and the slave device periodically communicate with each other.

14. The method according to claim 12, wherein stopping of the motion of the slave device is implemented by interrupting power to be applied to one of the drive units that drives at least one joint of the slave device.

15. A monitoring device connected to a master device and a slave device or a surgical robot, the monitoring device comprising:
a signal collector configured to collect a control signal and drive signals, control signal being transmitted from the master device to the slave device, and the drive signals being transmitted from the slave device to a plurality of drive units associated therewith;
a signal analyzer configured to analyze the control signal and the drive signals to detect if any of the control signal and the drive signals are abnormal; and
a controller configured to stop a motion of the slave device if the controller detects that one or more of the control signal and the drive signals are abnormal, wherein
the signal collector, the signal analyzer and the controller of the monitoring device are electrically connected together.

16. The monitoring device according to claim 15, further comprising:
a brake signal generator to generate a brake signal to stop a motion of the slave device if an abnormal signal is detected.

17. The monitoring device according to claim 16, wherein the controller of the monitoring device selectively stops a motion of the slave device according to whether it is determined a controller of the slave device has malfunctioned.

18. The monitoring device according to claim 17, wherein if it is determined the controller of the slave device has not malfunctioned, the controller of the monitoring device transmits a brake signal generated by the brake signal generator to the slave device to direct the controller of the slave device to stop the motion of the slave device.

19. The monitoring device according to claim 17, wherein if it is determined the controller of the slave device has malfunctioned, the controller of the monitoring device directly controls an emergency brake unit of the slave device to interrupt power applied to at least one of the drive units of the slave device, to stop the motion of the slave device.

* * * * *